United States Patent
Sreeramagiri et al.

(10) Patent No.: US 10,544,096 B2
(45) Date of Patent: Jan. 28, 2020

(54) CONTINUOUS METHODS OF MANUFACTURE OF 2-ARYL-3,3-BIS(4-HYDROXYARYL) PHTHALIMIDINES, AND POLYMERS DERIVED THEREFROM

(71) Applicant: SABIC GLOBAL TECHNOLOGIES B.V., Bergen Op Zoom (NL)

(72) Inventors: Sivakumar Sreeramagiri, Bangalore (IN); Deshmukh Sandesh Shivajirao, Bangalore (IN); Samir Anapat, Bangalore (IN); Vishal Keshaorao Karmore, Bangalore (IN); Sanjay Katrekar, Bangalore (IN); Alok Pal, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 16/316,539

(22) PCT Filed: Jul. 12, 2017

(86) PCT No.: PCT/US2017/041618
§ 371 (c)(1),
(2) Date: Jan. 9, 2019

(87) PCT Pub. No.: WO2018/013623
PCT Pub. Date: Jan. 18, 2018

(65) Prior Publication Data
US 2019/0308937 A1    Oct. 10, 2019

(30) Foreign Application Priority Data
Jul. 13, 2016   (IN) .............. 201611023923

(51) Int. Cl.
    C07D 209/46    (2006.01)
    C07D 209/44    (2006.01)
    C08G 64/30     (2006.01)
    C08G 64/12     (2006.01)

(52) U.S. Cl.
    CPC ......... *C07D 209/44* (2013.01); *C07D 209/46* (2013.01); *C08G 64/12* (2013.01); *C08G 64/307* (2013.01)

(58) Field of Classification Search
    CPC .................................................. C07D 209/46
    See application file for complete search history.

(56) References Cited

U.S. PATENT DOCUMENTS

| 2,522,939 | A | 9/1950 | Gamrath |
| 7,135,577 | B2 | 11/2006 | Rai et al. |
| 7,884,220 | B2 | 2/2011 | Xu et al. |
| 9,051,463 | B2 * | 6/2015 | Uno ............ C08L 69/00 |

FOREIGN PATENT DOCUMENTS

| WO | 2008115252 A1 | 9/2008 |
| WO | 2010067330 A1 | 6/2010 |
| WO | 2015115252 A1 | 8/2015 |

OTHER PUBLICATIONS

International Search Report; International Application No. PCT/US2017/041618: International Filing Date—Jul. 12, 2017; dated Oct. 12, 2017. 6 pages.
Sabnis, "A Facile Synthesis of Phthalein Indicator Dyes," Tetrahedron Letters 50 (2009) pp. 6261-6263, three pages.
Written Opinion; International Application No. PCT/US2017/041618; International Filing Date—Jul. 12, 2017; dated Oct. 12, 2017. 7 pages.

* cited by examiner

*Primary Examiner* — Laura L Stockton
(74) *Attorney, Agent, or Firm* — Cantor Colburn LLP

(57) ABSTRACT

A continuous method for the manufacture of a 2-aryl-3,3-bis(hydroxyaryl)phthalimidine comprising continuously heating an anhydride with a phenol in the presence of a catalyst and a first co-catalyst, to form a first reaction mixture comprising a phenolphthalein compound; precipitating the phenolphthalein compound; combining a primary arylamine with an acid catalyst and a second co-catalyst to form a second reaction mixture; adding the phenolphthalein compound to the second reaction mixture; continuously heating the second reaction mixture to provide a third reaction mixture comprising a crude phthalimidine; and treating the crude phthalimidine to remove aminophenol and purify the phthalimidine is provided.

20 Claims, No Drawings

CONTINUOUS METHODS OF MANUFACTURE OF 2-ARYL-3,3-BIS(4-HYDROXYARYL) PHTHALIMIDINES, AND POLYMERS DERIVED THEREFROM

CROSS REFERENCE TO RELATED APPLICATIONS

This application is a National Stage application of PCT/US17/041618, filed Jul. 12, 2017, which is incorporated by reference in its entirety herein, and which claims the benefit of IN Application No. 201611023923, filed Jul. 13, 2016.

BACKGROUND

This disclosure relates to methods for the manufacture of 2-aryl-3,3-bis(4-hydroxyaryl)phthalimidines.

Production of 2-phenyl-3,3-bis(4-hydroxyphenyl)phthalimidine (also known as N-phenyl phenolphthalein bisphenol (PPPBP) or 3,3-bis(4-hydroxyphenyl)-2-phenylisoindolin-1-one)) can be synthesized in two-step batch processes. The first step is making phenolphthalein (PP), by reacting phthalic anhydride with phenol in the presence of zinc chloride and chlorosulphonic acid as a co-catalyst at elevated temperature in a batch reactor, as described, for example, in U.S. Pat. No. 2,522,939. The purification and isolation of phenolphthalein is also performed batch-wise, for example as described in U.S. Patent Publication 2008/0177091, where the reaction mass is transferred to two or more additional vessels, filtered (sometimes in separate batches) and isolated. The second synthesis step is the reaction of the PP with aniline in the presence of an acid, followed by isolation to provide a crude product, as described, for example, in U.S. Pat. No. 8,809,486. The solid crude PPPBP is obtained after filtration and washing with water. Purification of crude PPPBP is usually also conducted in a batch process, for example as described in U.S. Pat. Nos. 7,135,577, 7,563,817, and 7,884,220. The total process can involve eight, ten, or more manual interventions.

There accordingly remains a need for improved methods for the manufacture of 2-phenyl-3,3-bis(4-hydroxyphenyl) phthalimidine, and in particular PPPBP.

BRIEF SUMMARY

A method for the manufacture of a 2-aryl-3,3-bis(hydroxyaryl)phthalimidine of formula (I)

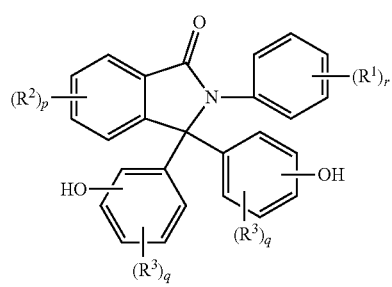
(I)

the method comprising: continuously heating an anhydride of formula (II)

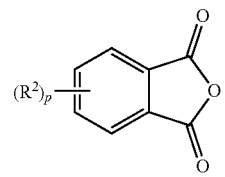
(II)

with a phenol of formula (III)

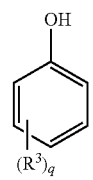
(III)

in the presence of a catalyst and a first co-catalyst, to form a first reaction mixture comprising a phenolphthalein compound of formula (IV)

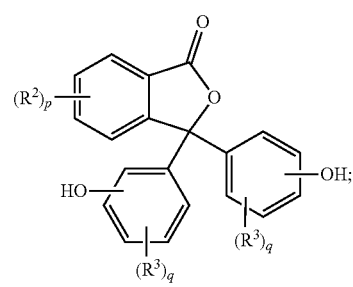
(IV)

continuously combining the first reaction mixture with sodium bisulfite and an organic solvent effective to dissolve the phenolphthalein compound of formula (IV) and reduce the temperature of the first reaction mixture; treating the first reaction mixture with an adsorbent to remove color; precipitating the phenolphthalein compound of formula (IV); continuously combining a primary arylamine of formula (V)

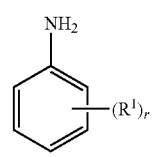
(V)

with an acid and a second co-catalyst to form a second reaction mixture; adding the phenolphthalein compound of formula (IV) to the second reaction mixture; continuously heating the second reaction mixture to provide a third reaction mixture comprising a crude phthalimidine of formula (I); continuously combining the third reaction mixture with an aqueous base to form a first aqueous stream; continuously extracting the first aqueous stream with an aminoaryl compound of formula (VI)

$(R^4)(R^5)N-Ar(R^6)_s$  (VI)

to provide an organic stream and a second aqueous stream comprising a crude phthalimidine of formula (I); continuously removing the aminoaryl compound of formula (VI) from the second aqueous stream to provide a third aqueous stream; continuously contacting the third aqueous stream with activated charcoal to provide a fourth aqueous stream; continuously precipitating the phthalimidine of formula (I) from the fourth aqueous stream to provide a slurry; continuously concentrating the slurry and separating a wet solid comprising the phthalimidine of formula (I) from the concentrated slurry; continuously triturating the wet solid comprising the 2-aryl-3,3-bis(hydroxyaryl)phthalimidine of formula (I) with an aqueous methanol solution to provide a triturated solid comprising the 2-aryl-3,3-bis(hydroxyaryl) phthalimidine of formula (I); and isolating the triturated solid to provide a purified 2-aryl-3,3-bis(hydroxyaryl) phthalimidine of formula (I), wherein in formulas (I), (II), (III), (IV), (V), and (VI) each occurrence of $R^1$ is independently a phenyl or a $C_{1-25}$ hydrocarbyl, preferably a phenyl or a $C_{1-6}$ alkyl, more preferably a $C_{1-3}$ alkyl, each occurrence of $R^2$ and $R^3$ is independently a $C_{1-25}$ hydrocarbyl or halogen, preferably a $C_{1-6}$ alkyl, more preferably a $C_{1-3}$ alkyl, and each $R^4$ and $R^5$ is independently a hydrogen or $C_{1-25}$ hydrocarbyl, preferably a hydrogen or $C_{1-6}$ alkyl, more preferably a hydrogen, Ar is a $C_{6-12}$ aromatic ring optionally comprising up to three heteroatoms in the ring, preferably a $C_6$ or a $C_{12}$ aromatic ring, each $R^6$ is independently a halogen, nitro, cyano, or $C_{1-25}$ hydrocarbyl, preferably a $C_{1-6}$ alkyl, more preferably a $C_{1-3}$ alkyl, and r, p, q, and s are each independently 0-4, more preferably 0 or 1, preferably 0 is provided.

A method for the manufacture of a polycarbonate, comprising manufacturing the 2-aryl-3,3-bis(4-hydroxyaryl) phthalimidine of formula (I) in accordance with a provided method; and polymerizing the 2-aryl-3,3-bis(4-hydroxyaryl) phthalimidine of formula (I) in the presence of a carbonate source is provided.

The above described and other features are exemplified by the following detailed description.

DETAILED DESCRIPTION

The present disclosure is generally directed to continuous or semi-continuous methods for producing phenolphthalein derivatives, in particular 2-aryl-3,3-bis(4-hydroxyaryl) phthalimidines, which are suitable for use as monomers or comonomers for preparing polycarbonates and other polymers. In some embodiments, provided is a continuous process for producing phenolphthalein, and a continuous process for producing 2-phenyl-3,3-bis(4-hydroxyphenyl) phthalimidine (PPPBP) and other 2-aryl-3,3-bis(4-hydroxyaryl)phthalimidines using no or a minimum of handling of solids during the process. This process can increase throughput, save energy consumption, and reduce raw material usage. The procedures in the method for forming phenolphthalein and PPPBP are further described below.

The 2-aryl-3,3-bis(4-hydroxyaryl)phthalimidines produced in accordance with these methods can be used in the manufacture of polycarbonates and other polymers. The 2-aryl-3,3-bis(4-hydroxyaryl)phthalimidines produced in accordance with these methods can have improved properties, such as a lower level of aminophenol impurity. The methods described to manufacture and purify 2-aryl-3,3-bis (4-hydroxyaryl)phthalimidines can further have a shorter reaction time as compared to previous methods, as well as reducing or eliminating the need for carbon adsorbents for impurity removal.

The 2-aryl-3,3-bis(4-hydroxyaryl)phthalimidines produced in accordance with this disclosure are of formula (I):

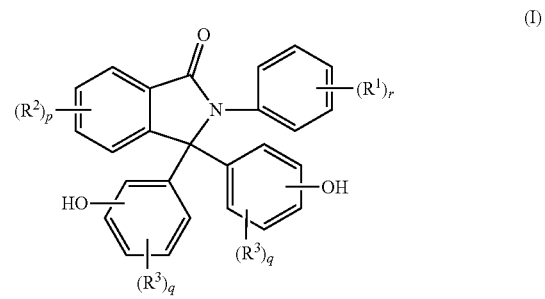

wherein each $R^1$ is independently a phenyl or a $C_{1-25}$ hydrocarbyl, each $R^2$ and $R^3$ is independently a $C_{1-25}$ hydrocarbyl or halogen, and r, p, and q are each independently 0-4. In some embodiments, each $R^1$ is independently a phenyl or a $C_{1-6}$ alkyl, each $R^2$ and $R^3$ is independently a $C_{1-6}$ alkyl, and r, p, and q are each independently 0 or 1. In some embodiments, $R^1$ is phenyl or a $C_{1-3}$ alkyl group, r and p are each independently 0-4. In some embodiments, r and p are each independently 0 or 1. In some embodiments, each q is 0, and $R^2$ is a $C_{1-3}$ alkyl group or a halogen. In still other embodiments, r, p, and q are each 0.

In an embodiment, a 2-aryl-3,3-bis(4-hydroxyaryl)phthalimidine is of formula (IA)

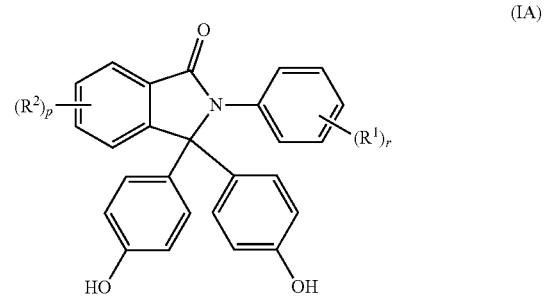

wherein $R^1$ is a $C_{1-3}$ alkyl, $R^2$ is a $C_{1-3}$ alkyl or a halogen, p is 0 or 1, and r is 0 or 1. In some embodiments, each of p and r is zero.

When each of p, q, and r is 0 in formulas (I) and (IA), the 2-aryl-3,3-bis(4-hydroxyaryl)phthalimidine is 2-phenyl-3,3-bis(4-hydroxyphenyl)-2-phthalimidine having formula (IB)

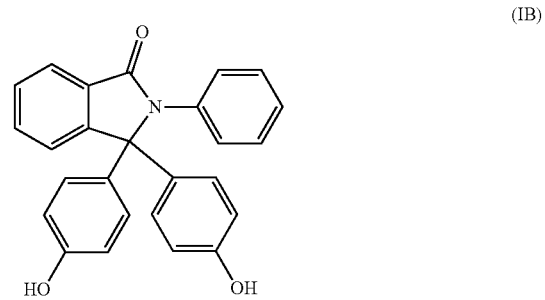 [SMILES: O=C1c2ccccc2C(c2ccc(O)cc2)(c2ccc(O)cc2)N1c1ccccc1]

In an embodiment, the process comprises manufacture of phenolphthalein, purification of the phenolphthalein, manufacture of the 2-aryl-3,3-bis(hydroxyaryl)phthalimidine of formula (I) using the purified phenolphthalein, and purification of the 2-aryl-3,3-bis(hydroxyaryl)phthalimidine of formula (I), wherein each step is conducted as a continuous process. In another embodiment, the phenolphthalein can be formed using other methods, such as those described in U.S. Pat. No. 8,809,486, and used in the continuous method to form PPPBP or other phthalimidines. The PPPBP or other phthalimidines are purified as described herein to contain the desired level of aminophenol, and other desired product specifications.

Thus, the first step of an embodiment comprises continuously heating an anhydride of formula (II)

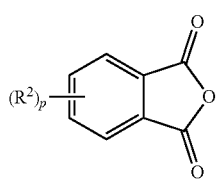
(II)

with a phenol of formula (III)

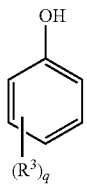
(III)

in the presence of a catalyst and a first co-catalyst, to form a first reaction mixture comprising a phenolphthalein compound of formula (IV)

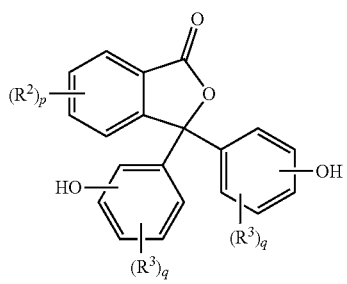
(IV)

wherein $R^2$, $R^3$, and r, p, and q are each as defined in formula (I) and (IA).

In an embodiment, the amount of the phenol (III) can be greater than 2 molar equivalents of the anhydride of formula (II). In another embodiment, the amount of the phenol (III) can be 2-3 molar equivalents of the anhydride of formula (II).

Examples of catalysts suitable for the formation of phenolphthalein compound (IV) include a metal halogenate, an inorganic acid, thionyl chloride, and sulphuryl chloride. Exemplary metal halogenate catalysts include zinc chloride, aluminum chloride, and stannic chloride. Exemplary inorganic acids include hydrochloric acid, sulphuric acid, and methanesulfonic acid. A combination comprising at least one of any of the foregoing catalysts can be used. The catalyst can be present in the amount of 3 to 20 mole percent (mol %), or 5 to 14 mol %, based on the total moles of reactants, catalyst, and first co-catalyst. In an embodiment, the catalyst is zinc chloride, which can be present in an amount of 10 to 20 mol % based on the total moles of reactants, catalyst, and first co-catalyst.

The first co-catalyst can be chlorosulphonic acid, trichloroacetic acid, methanesulfonic acid, dodecylbenzenesulfonic acid, triflic acid, boron trifluoride, p-toluene sulphonyl chloride, or the like. A combination comprising at least one of any of the foregoing co-catalysts can be used. In an embodiment the co-catalyst is chlorosulphonic acid. The first co-catalyst can be present in the amount of 1 to 6 mol %, or 2 to 5 mol %, based on the total moles of reactants, catalyst, and first co-catalyst.

In an embodiment, the reaction of the phthalic anhydride (II) and the phenol (III) in the first reaction mixture can be conducted at a temperature of 75-180° C., at atmospheric pressure. In another embodiment, the reaction of the phthalic anhydride (II) and the phenol (III) in the first reaction mixture can be conducted at a temperature of 80-140° C., at atmospheric pressure. In an embodiment, the reaction time can be 3-40 hours. In another embodiment, the reaction time can be 5-30 hours. In another embodiment, the reaction time can be 8-20 hours. In some embodiments, the reaction is conducted at 135-180° C. over a period of less than 10 hours. In some embodiments, the reaction is conducted at 140-175° C. over a period of less than 10 hours. In some embodiments, the reaction is conducted at a temperature of 100-150° C. for 4-10 hours. In some embodiments, the reaction is conducted at a temperature of 115-140° C. for 4-10 hours The reaction of the phthalic anhydride (II) and the phenol (III) can optionally be conducted in an inert organic solvent. In other embodiments, no solvent is present. Particularly when no solvent is present, the phenolphthalein compound (IV) can be insoluble in the first reaction mixture.

When the phenolphthalein compound (IV) is insoluble in the first reaction mixture, the first reaction mixture can be continuously combined with a solvent effective to reduce the temperature of the first reaction mixture and to dissolve the phenolphthalein compound of formula (IV). Exemplary solvents include aqueous solvents, for example an aqueous alcohol such as methanol and water, ethanol and water, or acetone and water. In an embodiment, the ratio of organic solvent to water can be 50:50 to 95:5 by volume. In another embodiment, the ratio of organic solvent to water can be 80:20 to 95:5 by volume. The first reaction mixture can be contacted with sodium bisulfite along with the solvent at the stage to deoxidize the reaction mixture, stabilize the product, and hinder color formation, for example.

The cooled first reaction mixture can then be treated with an adsorbent to remove color to provide a decolorized solution comprising the phenolphthalein compound (IV). The adsorbent can be, for example, activated carbon or charcoal. In an embodiment, the treatment is also a continuous process, for example by passing the cooled first reaction mixture over a fixed bed containing the adsorbent.

The decolorized phenolphthalein compound (IV) is then continuously precipitated from the decolorized solution. In an embodiment, the precipitation is by the removal of the solvent for the phenolphthalein compound (IV). In a specific embodiment, 20-80% of the solvent is removed to provide a slurry, which can then be cooled to 0-20° C. to further precipitate phenolphthalein compound (IV). In another specific embodiment, 50-70% of the solvent is removed to provide a slurry, which can then be cooled to 5-10° C. to further precipitate phenolphthalein compound (IV). The precipitated solid can be removed from the slurry by a continuous filter, such as a rotary vacuum or belt filter. Optionally, the precipitated solid can be washed with water.

In an embodiment, at least some water is removed from the precipitated phenolphthalein (IV) before its use in the next step. The higher the amount of water remaining in the phenolphthalein (IV), the longer the cycle time in the synthesis of the final product. Accordingly, the precipitated phenolphthalein (IV) can be continuously dried to achieve the desired level of water, for example less than 15 wt % water, based on the weight of the dried phenolphthalein (IV). In an embodiment, the desired level of water is less than 2 wt %.

The precipitated phenolphthalein compound (IV) is then used in a continuous process to manufacture the 2-aryl-3,3-bis(hydroxyaryl)phthalimidine of formula (I). In that process, a primary arylamine of formula (V)

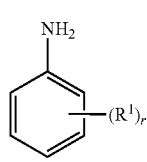

(V)

wherein $R^1$ and r are as described in formula (I), is continuously combined with an acid and a second co-catalyst to form a second reaction mixture. In an embodiment, the primary arylamine is aniline.

Exemplary acids include mineral acids. The mineral acids can be present in a fluid phase, for example, in a gaseous phase or in a liquid phase or in a combination of the gaseous and liquid phases. Non-limiting examples of mineral acids include hydrogen chloride liquid, hydrogen chloride gas, sulfuric acid, nitric acid, and the like. The acid can be present at a concentration of 0.5-1.5 molar equivalents of the phenolphthalein compound of formula (IV).

The mineral acid can form an amine salt from the reaction of the mineral acid with an amine, and the amine salt can function as a catalyst in the formation of phthalimidine (I). Examples of suitable amines for forming the acid catalysts include primary, secondary, and tertiary amines having any combination of aliphatic and aromatic groups bonded to the amine nitrogen. In an embodiment, the primary arylamine of formula (V) is used to form the amine salt.

In an embodiment, water is continuously removed from the second mixture. Thus, the acid catalyst and the primary arylamine (V) can be added to an optional solvent to form an initial second reaction mixture; and water can be removed from the initial second reaction mixture to provide a reduced water second reaction mixture. Removing water can be, for example by heating the second mixture above 120° C., or removing water as an azeotrope with the solvent or the primary arylamine of formula (V), e.g., aniline.

The second co-catalyst is a heterocyclic aromatic amine. In an embodiment, the heterocyclic aromatic amine has 5 to 10, or 5 to 6 atoms in the ring, and is unsubstituted or substituted with a halogen, nitro, cyano, $C_{1-6}$ alkyl, $C_{3-6}$ cycloalkyl, $C_{2-6}$ alkenyl, $C_{2-6}$ alkynyl, $C_1$-6 alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 atoms to form a fused aromatic ring wherein 1 or 2 of the atoms can be a nitrogen, or a combination comprising at least one of the foregoing substituents. In an embodiment, the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, $NR'_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing substituents. In embodiments, the heterocyclic aromatic amine is a pyrrole, an imidazole, a pyridine, an oxazole, an isoxazole, a thiazole, an azocine, an azecine, a quinolone, an isoquinoline, a purine, a carbazole, or a pyrimidine, wherein each of the foregoing can be unsubstituted or substituted with a halogen, nitro, cyano, $C_{1-6}$ alkyl, $C_{2-6}$ alkenyl, $C_{2-6}$ alkynyl, $C_{1-6}$ alkoxy, $C_{1-6}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-6}$ alkyl, $C_{6-10}$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing. In an embodiment, the ring is unsubstituted or substituted with a $C_{1-3}$ alkyl, $C_{1-3}$ alkoxy, $C_{1-3}$ alkoxycarbonyl, $C_{6-10}$ aryl, $C_{6-10}$ aryloxy, $C_{7-10}$ alkylarylene, $C_{7-10}$ arylalkylene, —$NR'_2$ wherein each R' is the same or different and is a hydrogen, $C_{1-3}$ alkyl, $C_6$ aryl, $C_{7-10}$ alkylarylene, or $C_{7-10}$ arylalkylene, or two adjacent carbon atoms are substituted with a divalent moiety having from 3 to 4 carbon atoms to form a fused aromatic ring, or a combination comprising at least one of the foregoing.

Examples of heterocyclic aromatic amines that can be used as the second co-catalyst include a pyrrole, an imidazole, an oxazole, an isoxazole, a thiazole, a pyridine, a pyrimidine, 4-dimethyl-aminopyridine, an azocine, or an azecine, and fused structures such as quinoline, isoquinoline, purine, or carbazole. In an embodiment, the heterocyclic aromatic amine co-catalyst is unsubstituted pyridine, unsubstituted imidazole, or 4-dimethylaminopyridine (DMAP).

In an embodiment, the heterocyclic aromatic amine can be present at a concentration of 0.005-0.5 molar equivalents of the phenolphthalein compound (IV). In an embodiment, the heterocyclic aromatic amine can be present at a concentration of 0.01-0.2 molar equivalents of the phenolphthalein compound (IV). The co-catalyst can be added at any time, for example with the aniline or to the second reaction mixture or to the initial second reaction mixture, or to the reduced water second reaction mixture. In an embodiment, the second co-catalyst is added to the reduced water second reaction mixture.

In an embodiment, the precipitated phenolphthalein compound (IV) is continuously added to the second reaction mixture, and is continuously added to the reduced water second reaction mixture. In an embodiment, the precipitated phenolphthalein compound (IV) with the second co-catalyst is continuously added to the second reaction mixture, and is continuously added to the reduced water second reaction mixture. An excess of the aryl amine over the phenolphthalein compound can be used to keep the reaction proceeding in a forward direction. For example, the primary arylamine can be present at a concentration of 3.0-5.0 molar equivalents of the phenolphthalein compound (IV).

The second reaction mixture containing the second co-catalyst and the phenolphthalein compound (IV) is continuously heated to provide a third reaction mixture comprising a crude phthalimidine (I). In an embodiment, the heating can occur at a temperature of 155-185° C., at atmospheric pressure. In an embodiment, the heating can occur at a temperature of 155-170° C., at atmospheric pressure. In an embodiment, the heating can be for 5-14 hours. In an embodiment, the heating can be for 6-12 hours.

Advantageously, the crude phthalimidine (I) is subsequently purified and isolated using a continuous process. The third reaction mixture can be continuously combined with an aqueous base to form a first aqueous stream. The first aqueous stream comprises the crude phthalimidine (I). The base can be sodium hydroxide, or another alkali metal hydroxide, or an alkaline earth metal hydroxide, for example.

The first aqueous stream can be continuously extracted with an aminoaryl compound of formula (VI)

$(R^4)(R^5)N—Ar(R^6)_s$ (VI)

wherein each $R^4$ and $R^5$ is independently a hydrogen or $C_{1-25}$ hydrocarbyl, each $R^6$ is independently a halogen, nitro, cyano, or $C_{1-25}$ hydrocarbyl, and s is 0-4. In an embodiment, each $R^4$ and $R^5$ is independently a hydrogen or $C_{1-6}$ alkyl, each $R^6$ is independently a $C_{1-6}$ alkyl, and s is 0 or 1. In an embodiment, each $R^4$ and $R^5$ is independently a hydrogen, each $R^6$ is a $C_{1-3}$ alkyl, and s is 0. In an embodiment, each $R^4$ and $R^5$ is a hydrogen, each $R^6$ is independently a $C_{1-3}$ alkyl, and s is 0 or 1. In an embodiment, the aminoaryl compound (VI) and the primary arylamine (V) is the same, for example each is aniline. In an embodiment, each $R^4$ and $R^5$ is independently a hydrogen or $C_{1-6}$ alkyl. In an embodiment, each $R^4$ and $R^5$ is a hydrogen. In an embodiment, each $R^6$ is independently a $C_{1-6}$ alkyl. In an embodiment, each $R^6$ is independently a $C_{1-3}$ alkyl. In an embodiment, s is 0 or 1. In an embodiment, s is 0.

Extraction of the first aqueous stream with the aminoaryl compound (VI) provides an organic stream comprising the aminoaryl compound (VI) and a second aqueous stream comprising residual aminoaryl compound (VI) and a salt of semi-crude phthalimidine (I). Residual aminoaryl compound (VI) is then removed from the second aqueous stream to provide a third aqueous stream. Removing the residual aminoaryl compound of formula (VI) from the second aqueous stream can be by azeotropic distillation or extraction with ethylene dichloride.

The third aqueous stream is continuously contacted with an adsorbent, such as activated charcoal, to remove trace impurities and decolorize the stream, which provides a fourth aqueous stream comprising a decolorized phthalimidine (I).

The decolorized phthalimidine (I) can then be continuously precipitated from the fourth aqueous stream to provide a slurry comprising the decolorized phthalimidine (I). Precipitation can be accomplished by acidification of the fourth aqueous stream, for example with a mineral acid.

The slurry comprising the decolorized phthalimidine (I) can then be continuously concentrated to provide a concentrated slurry (e.g., 60-80% solids), followed by separating a wet solid comprising the phthalimidine (I) from the concentrated slurry. Optionally, the wet solid can be re-slurried (e.g., 12-30% solids), for example a 90:10 methanol:water solution, refluxed at the boiling point of the solvent and cooled for example to −20° C., or 5-10° C. to further precipitate the phthalimidine (I). Alternatively, the wet solid comprising the phthalimidine (I) can be continuously triturated to provide a triturated solid comprising phthalimidine (I). The wet solid or the triturated solid can then be isolated, for example in a continuous crystallization, and the crystals are separated from the mother liquor, for example by continuous filtration, and optionally dried to provide a purified phthalimidine (I).

In an embodiment, the purified 2-aryl-3,3-bis(hydroxyaryl)phthalimidine of formula (I), can have a purity of greater than 99.9% by weight as determined by high performance liquid chromatography. In an embodiment, the purified 2-aryl-3,3-bis(hydroxyaryl)phthalimidine of formula (I) is PPPBP and the PPPBP has a purity of greater than 99.9% by weight as determined by high performance liquid chromatography. The phthalimidine (I) can comprise less than 500 parts per million (ppm) of the phenolphthalein compound (IV). The phthalimidine (I) can have an APHA color of less than 40. The phthalimidine (I) can comprise less than 50 parts per million of an aminophenol, for example an aminophenol of formula (VII)

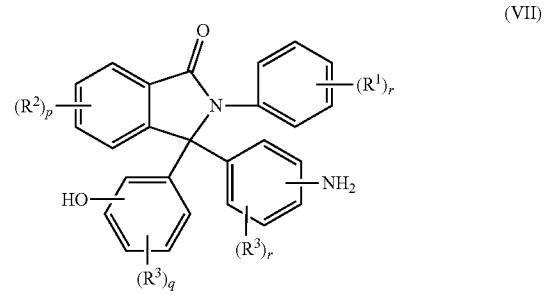

(VII)

wherein $R^1$, $R^2$, $R^3$, and r, p, and q are as described above in Formulas (I) and (IA).

A polymer comprising structural units derived from the 2-aryl-3,3-bis(4-hydroxyaryl) phthalimidine manufactured by the methods described herein is also provided. The polymer can be a polycarbonate. In an embodiment, the polymer is a copolycarbonate comprising units derived from the 2-aryl-3,3-bis(4-hydroxyaryl) phthalimidine of formula (I) and units derived from bisphenol A. A method for the manufacture of a polycarbonate, includes manufacturing the 2-aryl-3,3-bis(4-hydroxyaryl) phthalimidine of formula (I) in accordance with a method described herein; and polymerizing the 2-aryl-3,3-bis(4-hydroxyaryl) phthalimidine of formula (I) in the presence of a carbonate source The 2-aryl-3,3-bis(4-hydroxyaryl)phthalimidines, including the exemplary 2-phenyl-3,3-bis(4-hydroxyphenyl) phthalimidine (PPPBP), are commercially valuable monomers or comonomers for producing a variety of polymers formed by reactions of the phenolic OH groups of the 2-aryl-3,3-bis(4-hydroxyaryl)phthalimidines. Exemplary polymers that can be produced include homopolymers and copolymers of a polycarbonate, a polyestercarbonate, a polyester, a polyesteramide, a polyimide, a polyetherimide, a polyamideimide, a polyether, a polyethersulfone, a polycarbonate-polyorganosiloxane block copolymer, a copolymer comprising aromatic ester, ester carbonate, and carbonate repeat units, and a polyetherketone. An example of a copolymer comprising aromatic ester, estercarbonate, and carbonate repeat units is the copolymer produced by the reaction of a hydroxy-terminated polyester, such as the product of reaction of isophthaloyl chloride and terephthaloyl chloride with resorcinol, with phosgene and an aromatic dihydroxy compound, such as bisphenol A.

In some embodiments, polycarbonates having low color properties are synthesized, wherein the polycarbonates include structural units of formula (VIII)

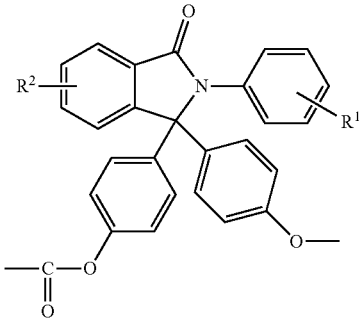

(VIII)

which are derived from a 2-aryl-3,3-bis(4-hydroxyaryl) phthalimidine of formula (I), wherein $R^1$ and $R^2$ are as described previously; and the C=O structural units are derived from a C=O donor such as a carbonic acid diester in a melt transesterification process, or phosgene in an interfacial process.

Specific polycarbonates are copolycarbonates having structural units derived from a phthalimidine compound of formula (I) and a dihydroxy compound of the formula HO—$R^1$—OH, in particular of formula (IX)

$$\text{HO-A}^1\text{-Y}^1\text{-A}^2\text{-OH} \quad (IX)$$

wherein each of $A^1$ and $A^2$ is a monocyclic divalent aromatic group and $Y^1$ is a single bond or a bridging group having one or more atoms that separate $A^1$ from $A^2$. In an exemplary embodiment, one atom separates $A^1$ from $A^2$. Specifically, each $R^1$ can be derived from a dihydroxy aromatic compound of formula (X)

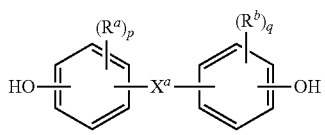

(X)

wherein $R^a$ and $R^b$ each represent a halogen or $C_{1-12}$ alkyl group and can be the same or different; and p and q are each independently integers of 0-4. $X^a$ represents a single bond or a bridging group connecting the two hydroxy-substituted aromatic groups, where the single bond or the bridging group and the hydroxy substituent of each $C_6$ arylene group are disposed ortho, meta, or para (specifically para) to each other on the $C_6$ arylene group. In an embodiment, the bridging group $X^a$ is —O—, —S—, —S(O)—, —S(O)$_2$—, —C(O)—, or a $C_{1-18}$ organic group. The $C_{1-18}$ organic group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic group. In some embodiments, p and q is each 1, and $R^a$ and $R^b$ are each a $C_{1-3}$ alkyl group, specifically methyl, disposed meta to the hydroxy group on each arylene group.

In an embodiment, $X^a$ is a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group. Exemplary groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene. In another embodiment, $X^a$ is a $C_{1-18}$ alkylene group, a $C_{3-18}$ cycloalkylene group, a fused $C_{6-18}$ cycloalkylene group, or a group of the formula —$B^1$—W—$B^2$— wherein $B^1$ and $B^2$ are the same or different $C_{1-6}$ alkylene group and W is a $C_{3-12}$ cycloalkylidene group or a $C_{6-16}$ arylene group.

Other useful aromatic dihydroxy compounds of the formula HO—$R^1$—OH include compounds of formula (XI)

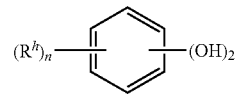

(XI)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0-4. The halogen is usually bromine.

Some illustrative examples of specific aromatic dihydroxy compounds include the following: 4,4'-dihydroxybiphenyl, 1,6-dihydroxynaphthalene, 2,6-dihydroxynaphthalene, bis(4-hydroxyphenyl)methane, bis(4-hydroxyphenyl) diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl) phenylmethane, 2,2-bis(4-hydroxy-3-bromophenyl) propane, 1,1-bis (hydroxyphenyl)cyclopentane, 1,1-bis(4-hydroxyphenyl)cyclohexane, 1,1-bis(4-hydroxyphenyl) isobutene, 1,1-bis(4-hydroxyphenyl)cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis (4-hydroxyphenyl)ether, bis(4-hydroxyphenyl)ether, bis(4-hydroxyphenyl)sulfide, bis(4-hydroxyphenyl)sulfoxide, bis (4-hydroxyphenyl)sulfone, 9,9-bis(4-hydroxyphenyl) fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula include 1,1-bis(4-hydroxyphenyl) methane, 1,1-bis(4-hydroxyphenyl) ethane, 2,2-bis(4-hydroxyphenyl) propane (hereinafter "bisphenol A" or "BPA"), 2,2-bis(4-hydroxyphenyl) butane, 2,2-bis(4-hydroxyphenyl) octane, 1,1-bis(4-hydroxyphenyl) propane, 1,1-bis(4-hydroxyphenyl) n-butane, 2,2-bis(4-hydroxy-2-methylphenyl) propane, 1,1-bis(4-hydroxy-t-butylphenyl) propane, 3,3-bis(4-hydroxyphenyl) phthalimidine, and 1,1-bis(4-hydroxy-3-methylphenyl)cyclohexane (DMBPC). Combinations comprising at least one of the foregoing dihydroxy compounds can also be used. In one specific embodiment, the polycarbonate is a linear homopolymer derived from bisphenol A, in which each of $A^1$ and $A^2$ is p-phenylene and $Y^1$ is isopropylidene in formula (3).

Exemplary carbonic acid diesters useful in the formation of the polycarbonates in a melt transesterification process are of formula (XII)

$$(ZO)_2C=O \qquad (XII)$$

wherein each Z is independently an unsubstituted or substituted $C_{1-12}$ alkyl radical, or an unsubstituted or substituted $C_{6-22}$ aryl radical. Examples of carbonic acid diesters include, but are not limited to, ditolyl carbonate, m-cresyl carbonate, dinaphthyl carbonate, diphenyl carbonate, diethyl carbonate, dimethyl carbonate, dibutyl carbonate, dicyclohexyl carbonate, and combinations thereof. Diphenyl carbonate is widely used as a carbonic acid diester due to its low cost and ready availability on a commercial scale. Use of activated aromatic carbonates that are more reactive than diphenyl carbonate is also contemplated. Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures are also contemplated. Exemplary ester-substituted diaryl carbonates include, but are not limited to, bis(methylsalicyl)carbonate (CAS Registry No. 82091-12-1) (also known as BMSC or bis(o-methoxycarbonylphenyl) carbonate), bis(ethyl salicyl)carbonate, bis(propyl salicyl) carbonate, bis(butylsalicyl) carbonate, bis(benzyl salicyl) carbonate, bis(methyl 4-chlorosalicyl)carbonate, and the like. In some embodiments, BMSC is used in the melt transesterification process.

The melt transesterification process is generally carried out by combining a catalyst, the carbonic acid diester of formula (IX), the phthalimidine compound of formula (I), and optionally a dihydroxy comonomer; and mixing the reaction mixture under reactive conditions for a time period effective to produce the polycarbonate product. Exemplary melt transesterification catalysts include alkali metal compounds, alkaline earth metal compounds, tetraorganoammonium compounds, tetraorganophosphonium compounds, and combinations comprising at least one of the foregoing catalysts. Specific examples of alkali metal compounds or alkaline earth metal compounds include, but are not limited to, sodium hydroxide, potassium hydroxide, calcium hydroxide, magnesium hydroxide, sodium bicarbonate, potassium bicarbonate, sodium carbonate, potassium carbonate, lithium carbonate, sodium acetate, potassium acetate, sodium stearate, potassium stearate, sodium hydroxyborate, sodium phenoxyborate, sodium benzoate, potassium benzoate, lithium benzoate, disodium hydrogen phosphate, dipotassium hydrogen phosphate, dilithium hydrogen phosphate, disodium salts, dipotassium salts, and dilithium salts of bisphenol A, and sodium salts, potassium salts, lithium salts of phenol, and the like. Specific examples of tetraorganoammonium compounds and tetraorganophosphonium compounds include, but are not limited to tetramethylammonium hydroxide, tetrabutylammonium hydroxide, tetraethylphosphonium hydroxide, tetrabutylphosphonium acetate, tetrabutylphosphonium hydroxide, and the like.

In some embodiments, the catalyst is tetrabutylphosphonium acetate. In an alternative embodiment, the catalyst comprises a mixture of an alkali metal salt or alkaline earth metal salt with at least one quaternary ammonium compound, at least one quaternary phosphonium compound, or a mixture thereof. For example, the catalyst can be a mixture of sodium hydroxide and tetrabutylphosphonium acetate. In another embodiment, the catalyst is a mixture of sodium hydroxide and tetramethylammonium hydroxide. In yet another embodiment, the catalyst comprises the salt of a non-volatile inorganic acid, for example alkali metal salts of phosphites; alkaline earth metal salts of phosphites; alkali metal salts of phosphates; and alkaline earth metal salts of phosphates, including but not limited to $NaH_2PO_3$, $NaH_2PO_4$, $Na_2H_2PO_3$, $KH_2PO_4$, $CsH_2PO_4$, $Cs_2H_2PO_4$, or a mixture thereof. In some embodiments, the transesterification catalyst comprises both the salt of a non-volatile acid and a basic co-catalyst such as an alkali metal hydroxide. This concept is exemplified by the use of a combination of $NaH_2PO_4$ and sodium hydroxide as the transesterification catalyst.

Any of the catalysts disclosed above can be used as combinations of two or more substances. Moreover, the catalyst can be added in a variety of forms. For example, the catalyst can be added as a solid as a powder, or it can be dissolved in a solvent, for example, in water or alcohol. The total catalyst composition can be about $1 \times 10^{-7}$ to about $2 \times 10^{-3}$ moles, and in other embodiments, about $1 \times 10^{-6}$ to about $4 \times 10^{-4}$ moles, for each mole of the combination of, for example, the purified PPPBP and the aromatic dihydroxy comonomer.

The progress of the polymerization reaction can be monitored by measuring the melt viscosity or the weight average molecular weight of the reaction mixture using techniques known in the art such as gel permeation chromatography. These properties can be measured by taking discreet samples or can be measured on-line. After the desired melt viscosity or molecular weight is reached, the final polycarbonate product can be isolated from the reactor in a solid or molten form. The method of making polycarbonates as described in the preceding sections can be made in a batch or a continuous process.

In some embodiments, the melt-polymerized polycarbonate is prepared in an extruder in the presence of one or more catalysts. The reactants for the polymerization reaction can be fed to the extruder in powder or molten form. In some embodiments, the reactants are dry blended prior to addition to the extruder. The extruder can be equipped with pressure reducing devices (e.g., vents) that serve to remove the activated phenol byproduct and thus drive the polymerization reaction toward completion. The molecular weight of the polycarbonate product can be manipulated by controlling, among other factors, the feed rate of the reactants, the type of extruder, the extruder screw design, and configuration, the residence time in the extruder, the reaction temperature, and the pressure reducing techniques present on the extruder. The molecular weight of the polycarbonate product can also depend upon the structures of the reactants and the catalyst employed.

Alternatively, the polycarbonates can be prepared by an interfacial polymerization process. Although the reaction conditions for interfacial polymerization can vary, an exemplary process generally involves dissolving or dispersing a dihydric phenol reactant in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., about 8-about 12. Exemplary water immiscible solvents include methylene chloride, 1,2-dichloroethane, chlorobenzene, toluene, and the like.

Exemplary carbonate precursors for interfacial polymerization include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary embodiment, an interfacial polymerization reaction to form carbonate linkages uses phosgene as a carbonate precursor, and is referred to as a phosgenation reaction.

Among the phase transfer catalysts that can be used for interfacial polymerization are tetraorganoammonium compounds and tetraorganophosphonium compounds of the formula $(R_3)_4Q^+X$, wherein each $R_3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, Br$^-$, a $C_{1-8}$ alkoxy group or a $C_{6-18}$ aryloxy group. An effective amount of a phase transfer catalyst can be about 0.1- about 10 wt % based on the weight of bisphenol in the phosgenation mixture. In another embodiment an effective amount of phase transfer catalyst can be about 0.5- about 2 wt % based on the weight of bisphenol in the phosgenation mixture.

All types of polycarbonate end groups are contemplated as being useful in the polycarbonate composition, provided that such end groups do not significantly adversely affect desired properties of the compositions. Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate. Exemplary chain stoppers include certain mono-phenolic compounds, mono-carboxylic acid chlorides, or mono-chloroformates.

The interfacial method described above can be suitably adapted to produce polycarbonates through the intermediate formation of 2-aryl-3,3-bis(4-hydroxyaryl)phthalimidine bischloroformate. This method is sometimes called the bischloroformate polymerization method. In some embodiments, the method comprises reacting a 2-aryl-3,3-bis(4-hydroxyaryl)phthalimidine with phosgene in an organic solvent, and then reacting the bischloroformate either with a 2-aryl-3,3-bis(4-hydroxyaryl)phthalimidine, or an aromatic dihydroxy compound in the presence of an acid acceptor and an aqueous base to form the polycarbonate. The interfacial polymerization method and the bischloroformate polymerization method can be carried in a batch or a continuous mode using one or more reactor systems. To carry out the process in a continuous mode, one or more continuous reactors, such as for example, a tubular reactor can be used. In some embodiments, the continuous method comprises introducing into a tubular reactor system phosgene, at least one solvent (example, methylene chloride), at least one bisphenol, aqueous base, and optionally one or more catalysts (example, a trialkylamine) to form a flowing reaction mixture. The flowing mixture is then passed through the tubular reactor system until substantially all of the phosgene has been consumed. The resulting mixture is next treated with a mixture comprising an aqueous base, at least one endcapping agent, optionally one or more solvents, and at least one catalyst. The endcapped polycarbonate thus formed is continuously removed from the tubular reactor system.

The processes disclosed herein can advantageously be used to prepare, for example, PPPBP homopolycarbonate and copolycarbonates having a weight average molecular weight (Mw) of about 3,000- about 150,000 Daltons and a glass transition temperature (Tg) of about 800° C.- about 300° C. The number average molecular weights (Mn) of the homopolycarbonate and copolycarbonates can be from about 1,500- about 75,000 Daltons.

Polymers comprising structural units derived from the phthalimidines, in particular PPPBP can be used to manufacture polymer blends comprising the polymer and at least one other thermoplastic polymer. The at least one other thermoplastic polymer includes vinyl polymers, acrylic polymers, polyacrylonitrile, polystyrenes, polyolefins, polyesters, polyurethanes, polyamides, polysulfones, polyimides, polyetherimides, polyphenylene ethers, polyphenylene sulfides, polyether ketones, polyether ether ketones, ABS polymers, polyethersulfones, poly(alkenylaromatic) polymers, polybutadiene, polyacetals, polycarbonates, polyphenylene ethers, ethylene-vinyl acetate copolymers, polyvinyl acetate, liquid crystal polymers, ethylene-tetrafluoroethylene copolymer, aromatic polyesters, polyvinyl fluoride, polyvinylidene fluoride, polyvinylidene chloride, tetrafluoroethylene, polycarbonate-polyorganosiloxane block copolymers, copolymers comprising aromatic ester, estercarbonate, and carbonate repeat units, and combinations comprising at least one of the foregoing polymers.

The polymers and polymer blends described hereinabove are valuable for producing articles. In some embodiments, an article comprises a polymer comprising structural units derived from a 2-aryl-3,3-bis(4-hydroxyaryl)phthalimidine of formula (I) prepared by following the process described above.

Polymers, particularly polycarbonate homopolymers and copolymers comprising structural units derived from the high purity 2-aryl-3,3-bis(4-hydroxyaryl)phthalimidine in general, and PPPBP in particular exhibit lower visual coloration. As such, these polycarbonate polymers are useful for producing articles having a number of useful properties, including lower visual color, among others. The polycarbonate homopolymers and copolymers have high glass transition temperatures of higher than or equal to about 180° C. One of the unique properties of these polycarbonates, especially those that have glass transition temperatures of greater than or equal to about 180° C. is that during melt processing they exhibit a shear-thinning behavior. That is, the polymers have the ability to flow under an applied shear. Therefore, standard melt processing equipment used for BPA polycarbonates can advantageously be used for producing articles. The polycarbonates also have high transparency, as measured by percent light transmission, of greater than or equal to about 85 percent.

In addition to the polymer, the thermoplastic compositions comprising the polymers can include various additives ordinarily incorporated into polymer compositions of this type, with the proviso that the additive(s) are selected so as to not significantly adversely affect the desired properties of the thermoplastic composition, in particular low color. Such additives can be mixed at a suitable time during the mixing of the components for forming the composition. The additive can be soluble or non-soluble in polycarbonate. The additive composition can include an impact modifier, flow modifier, filler (e.g., a particulate polytetrafluoroethylene (PTFE), glass, carbon, mineral, or metal), reinforcing agent (e.g., glass fibers), antioxidant, heat stabilizer, light stabilizer, ultraviolet (UV) light stabilizer, UV absorbing additive, plasticizer, lubricant, release agent (such as a mold release agent), antistatic agent, anti-fog agent, antimicrobial agent, colorant (e.g., a dye or pigment), surface effect additive, radiation stabilizer, flame retardant, anti-drip agent (e.g., a PTFE-encapsulated styrene-acrylonitrile copolymer (TSAN)), or a combination comprising at least one or more of the foregoing. For example, a combination of a heat stabilizer, mold release agent, and ultraviolet light stabilizer can be used. In general, the additives are used in the amounts generally known to be effective. For example, the total amount of the additive composition (other than any impact modifier, filler, or reinforcing agent) can be 0.001-10.0 wt %, or 0.01-5 wt %, each based on the total weight of the polymer in the composition.

The methods described herein are further illustrated by the following non-limiting examples.

EXAMPLES

Example 1 (Comparative)

A process for production of PPPBP is optionally a two-step process, where the first step is making PP in a batch reactor with a cycle time of 15-20 hours (hrs). Phthalic anhydride is reacted with phenol in the presence of $ZnCl_2$ as a catalyst and chlorosulfonic acid (CSA) as a co-catalyst. The purification and isolation of phenolphthalein is also performed batch-wise where the phenolphthalein reaction mass is cooled to 65° C. and partially dissolved in methanol-water mixture to make the reaction mass flow. The reaction mass is then transferred to another vessel and completely dissolved in a 90% methanol in water, and further treated with activated charcoal and sodium bisulfite. The slurry reaction mass is then filtered to remove the charcoal and collected in a separate vessel. The reaction mass is then boiled away to evaporate more than 50% of the solvent and then cooled to induce to precipitation of the phenolphthalein. The slurry is then separated for solid isolation using multiple centrifuge batches. The product is washed in a centrifuge with hot water and dried in batches.

The second chemistry step is the reaction of phenolphthalein with aniline catalyzed by hydrochloric acid in a reaction that can be conducted for up to 50 hrs. The reaction mixture is then cooled to room temperature and treated with hydrochloric acid and water. The solid crude product is obtained after filtration and washing with water. Crude PPPBP has aminophenol (AP) as the major impurity. Removal of the AP impurity is performed to reduce the AP concentration to less than 50 parts per million (ppm), and can require multiple steps wherein the crude product is subjected to multiple treatments with activated charcoal in an alkaline medium to remove AP impurity. After charcoal treatment, the PPPBP is then isolated from the base solution by neutralization. Solid PPPBP is recovered by batch filtration. The solid PPPBP is then subjected to methanol trituration for removal of unreacted residual phenolphthalein followed by filtration, hot water wash, and drying. The final PPPBP product is obtained with an overall yield of 89-90% with respect to phenolphthalein.

Example 2

A exemplary continuous process as is described herein. Phenolphthalein is made by continuously feeding the reactants phthalic anhydride, phenol, and the catalyst $ZnCl_2$, into a mixing vessel operated at a temperature of about 60° C. to form a homogeneous mixture, and then pumped to a continuous flow reactor (CFR). The co-catalyst chlorosulfonic acid is continuously injected at the inlet of the CFR or optionally in parts along the length of CFR. The CFR is maintained at a temperature of about 120-140° C. under pressure to keep the reaction mixture in a liquid phase. The reaction mass is kept in CFR for a residence time of 3-5 hrs. The reaction mass is then fed to a continuous stirred reactor (CSTR) at 120-140° C. with residence time of 1-2 hrs and atmospheric pressure. The reactor stream from the CSTR is pumped and mixed with 90% methanol in water solvent along with sodium bisulfite in a static mixer, to rapidly reduce the temperature and dissolve the PP, and passed through a mixing vessel with a residence time of 0.5-1 hr. The solvent stream is then pumped through a bed of activated carbon to remove impurities, and superheated to about 120° C. using a super-heater. The pressurized stream is then flashed in a flash vessel which is supplemented with a high pressure circulatory heater in a recycle loop. The product stream, which is a slurry, is then cooled to 5-10° C. in a vessel to precipitate the product, and separated in a continuous filter (such as a rotary vacuum or belt filter), and washed with water. The washed solid is then dried in a continuous dryer, for example using hot gases. The dried phenolphthalein powder is then conveyed to the PPPBP manufacturing process.

A continuous filter, such as a belt filter, or a continuous pressure filter, allows removing some of the water from the phenolphthalein powder, prior to conveying the phenolphthalein to the next step.

Aniline and aqueous HCl are continuously mixed in a mixing vessel with a residence time of about 1 hr to form aniline hydrochloride salt. The resultant mass is fed in a falling film evaporator operated at atmospheric pressure (or optionally under vacuum) and 100-140° C. to dry the aniline solution. The evaporated water and aniline layer is separated and aniline is recycled back to storage. The dried liquid is cooled in a heat exchanger to the desired temperature (70-90° C.) and then a pyridine co-catalyst is added. The use of a co-catalyst can reduce the reaction time from greater than 35 hours to less than 10 hours.

The resulting mixture is continuously fed to the first of a series of 2 or 3 continuous stirred reactors (CSTRs). The other reactant, phenolphthalein powder (optionally dissolved in aniline hydrochloride), is continuously fed in the first CSTR. Together a combined minimum residence time of 8 hrs and temperature of 170° C. is provided in the series of reactors. The reaction mixture is then passed through a tubular flow reactor (TFR) with residence time of up to 2 hrs at a temperature of about 170° C. The stream flowing out of TFR is mixed with sufficient aqueous NaOH solution to neutralize the reaction in a reflux vessel with residence time of about 1 hr and maintained well below the boiling points of the stream to form a homogeneous aqueous alkaline stream. A liquid-liquid extraction step using a liquid extraction column is used to extract aminophenol impurity using aniline as a solvent. The outgoing organic aniline stream is then fed to recover the pure aniline using distillation or falling film evaporation. The aqueous stream containing the product PPPBP as sodium salt is then processed to remove aniline or organic solvent removal, e.g., by azeotrope distillation or extraction using ethylene dichloride. The organic stream is then sent for aniline and ethylene dichloride recovery, while the aqueous stream (free of organics) is passed through a bed of activated charcoal arranged in parallel and operated in switching mode to remove trace impurities. The resulting stream from the adsorption column is treated with aqueous HCl to precipitate the PPPBP product in vessel. The product can be concentrated using a mixer settler or hydro-cyclone or fed to a continuous filter like the belt of a rotary vacuum or other filter. The wet cake is then mixed with 90% methanol in water to re-slurry in a re-slurry vessel and cooled down (to 5-10° C.) in a vessel. The solids are separated and washed with hot water in a continuous filter. The mother liquor is sent to methanol recovery using a distillation column. The wet cake is then dried in a continuous drier using hot gases and the final purified product can be sent for packaging. The final product is of purity>99.9% by weight with an AP content of less than 50 ppm, a PP content of less than 500 ppm, and color as measured by APHA of less than 40.

The continuous operation for PPPBP production described converts a batch process into a continuous or semi-continuous process; reduces the batch solid isolation and manual operations and interventions required, while maintaining the product specifications of the current process; reduces utilization of raw materials compared to current practice and reduces the operational expenditure; reduces the equipment sizes required to meet the increased demand of production and uses less equipment; and reduces the manual material handling and allows for improvement in material losses, energy efficiency, quality consistency and better process control.

The methods and polymers are further illustrated by the following embodiments, which are non-limiting.

Embodiment 1

A method for the manufacture of a 2-aryl-3,3-bis(hydroxyaryl)phthalimidine of formula (I)

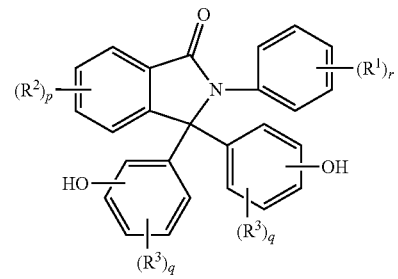

the method comprising: continuously heating an anhydride of formula (II)

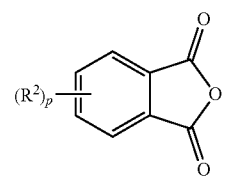

with a phenol of formula (III)

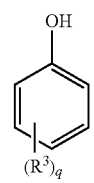

in the presence of a catalyst and a first co-catalyst, to form a first reaction mixture comprising a phenolphthalein compound of formula (IV)

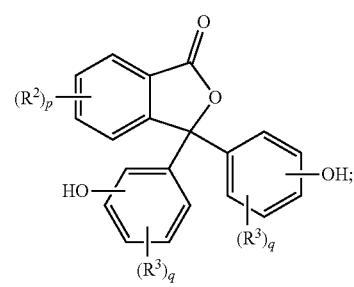

continuously combining the first reaction mixture with sodium bisulfite and an organic solvent effective to dissolve the phenolphthalein compound of formula (IV) and reduce the temperature of the first reaction mixture; treating the first reaction mixture with an adsorbent to remove color; precipitating the phenolphthalein compound of formula (IV); continuously combining a primary arylamine of formula (V)

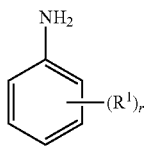 (V)

with an acid and a second co-catalyst to form a second reaction mixture; adding the phenolphthalein compound of formula (IV) to the second reaction mixture; continuously heating the second reaction mixture to provide a third reaction mixture comprising a crude phthalimidine of formula (I); continuously combining the third reaction mixture with an aqueous base to form a first aqueous stream; continuously extracting the first aqueous stream with an aminoaryl compound of formula (VI)

$$(R^4)(R^5)N-Ar(R^6)_s \qquad (VI)$$

to provide an organic stream and a second aqueous stream comprising a crude phthalimidine of formula (I); continuously removing the aminoaryl compound of formula (VI) from the second aqueous stream to provide a third aqueous stream; continuously contacting the third aqueous stream with activated charcoal to provide a fourth aqueous stream; continuously precipitating the phthalimidine of formula (I) from the fourth aqueous stream to provide a slurry; continuously concentrating the slurry and separating a wet solid comprising the phthalimidine of formula (I) from the concentrated slurry; continuously triturating the wet solid comprising the 2-aryl-3,3-bis(hydroxyaryl)phthalimidine of formula (I) with an aqueous methanol solution to provide a triturated solid comprising the 2-aryl-3,3-bis(hydroxyaryl) phthalimidine of formula (I); and isolating the triturated solid to provide a purified 2-aryl-3,3-bis(hydroxyaryl) phthalimidine of formula (I), wherein in formulas (I), (II), (III), (IV), (V), and (VI) each occurrence of $R^1$ is independently a phenyl or a $C_{1-25}$ hydrocarbyl, each occurrence of $R^2$ and $R^3$ is independently a $C_{1-25}$ hydrocarbyl or halogen, and each $R^4$ and $R^5$ is independently a hydrogen or $C_{1-25}$ hydrocarbyl, Ar is a $C_{6-12}$ aromatic ring optionally comprising up to three heteroatoms in the ring, each $R^6$ is independently a halogen, nitro, cyano, or $C_{1-25}$ hydrocarbyl, and r, p, q, and s are each independently 0-4.

Embodiment 2

The method of Embodiment 1, wherein each occurrence of $R^1$ is independently a phenyl or a $C_{1-6}$ alkyl, each occurrence of $R^2$ and $R^3$ is independently a $C_{1-6}$ alkyl, each $R^4$ and $R^5$ is independently a hydrogen or $C_{1-6}$ alkyl, Ar is a $C_6$ or a $C_{12}$ aromatic ring, each $R^6$ is independently a $C_{1-6}$ alkyl, and r, p, q, and s are each independently 0 or 1.

Embodiment 3

The method of Embodiment 1 or 2, wherein each occurrence of $R^1$ is independently a $C_{1-3}$ alkyl, each occurrence of $R^2$ and $R^3$ is independently a $C_{1-3}$ alkyl, and each $R^4$ and $R^5$ is independently a hydrogen, Ar is a $C_6$ aromatic ring, each $R^6$ is independently a $C_{1-3}$ alkyl, and r, p, q, and s are each independently 0.

Embodiment 4

The method of any one of more of Embodiments 1-3, wherein the anhydride of formula (II) is phthalic anhydride, the phenol of formula (III) is phenol, the catalyst is $ZnCl_2$, and the first co-catalyst is chlorosulfonic acid.

Embodiment 5

The method of any one or more of Embodiments 1-4, wherein the heating the first reaction mixture is at 100-150° C.

Embodiment 6

The method of any one or more of Embodiments 1-5, wherein the heating the first reaction mixture is at 115-140° C.

Embodiment 7

The method of any one or more of Embodiments 1-6, wherein the heating the first reaction mixture is for 4-10 hours.

Embodiment 8

The method of any one or more of Embodiments 1-7, wherein precipitating the phenolphthalein compound of formula (IV) comprises at least partially removing the solvent to form a slurry, and cooling the slurry.

Embodiment 9

The method of any one or more of Embodiments 1-8, further comprising washing the precipitated phenolphthalein compound of formula (IV).

Embodiment 10

The method of any one or more of Embodiments 1-9, further comprising drying the precipitated phenolphthalein compound of formula (IV).

Embodiment 11

The method of any one or more of Embodiments 1-10, wherein the primary arylamine of formula (V) is aniline, the acid catalyst is a mineral acid, the second co-catalyst is a heterocyclic aromatic amine.

Embodiment 12

The method of any one or more of Embodiments 1-11, wherein the primary arylamine of formula (V) is aniline, the acid catalyst is hydrochloric acid, the second co-catalyst is pyridine or 4-dimethylamino pyridine (DMAP).

Embodiment 13

The method of any one or more of Embodiments 1-12, wherein the heating the second reaction mixture is from 155-185° C.

Embodiment 14

The method of any one or more of Embodiments 1-13, wherein the heating the second reaction mixture is from 155-170° C.

Embodiment 15

The method of any one or more of Embodiments 1-14, wherein the heating the second reaction mixture is for 5-15 hours.

Embodiment 16

The method of any one or more of Embodiments 1-15, wherein the heating the second reaction mixture is for 6-12 hours.

Embodiment 17

The method of any one or more of Embodiments 1-16, wherein the phenol of formula (III) is present at a concentration of greater than 2 molar equivalents of the anhydride of formula (II).

Embodiment 18

The method of any one or more of Embodiments 1-17, wherein the phenol of formula (III) is present at a concentration of 2-3 molar equivalents of the anhydride of formula (II).

Embodiment 19

The method of any one or more of Embodiments 1-18, comprising adding the acid catalyst and the primary arylamine to form an initial second reaction mixture; removing water from the initial second reaction mixture to provide a reduced water second reaction mixture; and adding the phenolphthalein compound of formula (IV) and the second co-catalyst to the reduced water second reaction mixture to provide the second reaction mixture.

Embodiment 20

The method of any one or more of Embodiments 1-19, further comprising recycling the aminoaryl compound of formula (VI) from the organic stream.

Embodiment 21

The method of any one or more of Embodiments 1-10, wherein removing the residual aminoaryl compound of formula (VI) from the aqueous stream comprises azeotropic distillation or extraction with ethylene dichloride.

Embodiment 22

The method of any one or more of Embodiments 1-21, further comprising precipitating the phthalimidine of formula (I) from the reaction mixture.

Embodiment 23

The method of any one or more of Embodiments 1-22, wherein the 2-aryl-3,3-bis(hydroxyaryl)phthalimidine of formula (I) is of formula (IA)

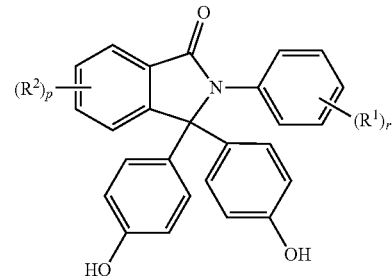

(IA)

wherein $R^1$ is a $C_{1-3}$ alkyl, $R^2$ is a $C_{1-3}$ alkyl or a halogen, p is 0 or 1, and r is 0 or 1.

Embodiment 24

The method of any one or more of Embodiments 1-23, wherein the 2-aryl-3,3-bis(hydroxyaryl)phthalimidine of formula (I) is 2-phenyl-3,3-bis(4-hydroxyphenyl)-2-phthalimidine.

Embodiment 25

The method of any one or more of Embodiments 1-24, comprising combining the phenolthelein compound of formula (IV) and the primary arylamine of formula (V) to form a combined reaction mixture; removing water from the combined reaction mixture to a level of less than 4 wt %.

Embodiment 26

A method for the manufacture of a 2-phenyl-3,3-bis(4-hydroxyphenyl)-2-phthalimidine of formula (IB)

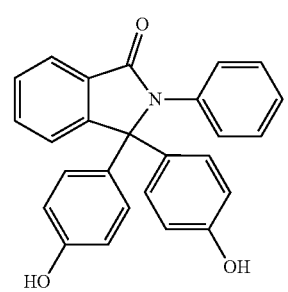

(IB)

the method comprising: continuously heating phthalic anhydride with phenol in the presence of $ZnCl_2$ and chlorosulfonic acid at 100-150° C. for 4-10 hours, to form a first reaction mixture comprising a phenolphthalein compound; continuously combining the first reaction mixture with sodium bisulfite and an organic solvent effective to dissolve the phenolphthalein compound and reduce the temperature of the first reaction mixture; treating the first reaction mixture with activated carbon or charcoal to remove color; precipitating the phenolphthalein compound by at least partially removing the solvent to form a slurry, and cooling the slurry; continuously combining aniline with hydrochloric acid and pyridine or 4-dimethylamino pyridine (DMAP) to form a second reaction mixture; adding the phenolphthalein compound to the second reaction mixture; continuously heating the second reaction mixture at 155-185° C. for 5-15 hours to provide a third reaction mixture comprising a crude phthalimidine of formula (IB); continuously combining the third reaction mixture with sodium hydroxide to form a first aqueous stream; continuously extracting the first aqueous stream with aniline to provide an organic stream and a second aqueous stream comprising a crude phthalimidine of formula (IB); continuously removing the aniline from the second aqueous stream to provide a third aqueous stream; continuously contacting the third aqueous stream with activated charcoal to provide a fourth aqueous stream; continuously precipitating the phthalimidine of formula (IB) from the fourth aqueous stream to provide a slurry; continuously concentrating the slurry and separating a wet solid comprising the phthalimidine of formula (IB) from the concentrated slurry; continuously triturating the wet solid comprising the 2-aryl-3,3-bis(hydroxyaryl)phthalimidine of formula (IB) with an aqueous methanol solution to provide a triturated solid comprising the 2-aryl-3,3-bis(hydroxyaryl)phthalimidine of formula (IB); and continuously isolating the triturated solid to provide a purified 2-aryl-3,3-bis(hydroxyaryl)phthalimidine of formula (IB).

Embodiment 26

A method for the manufacture of a polycarbonate, comprising manufacturing the 2-aryl-3,3-bis(4-hydroxyaryl) phthalimidine of formula (I) in accordance with any one or more of Embodiments 1-24; and polymerizing the 2-aryl-3,3-bis(4-hydroxyaryl) phthalimidine of formula (I) in the presence of a carbonate source.

The term "hydrocarbyl" is defined herein as a monovalent moiety formed by removing a hydrogen atom from a hydrocarbon. Representative hydrocarbyls are alkyl groups having 1-25 carbon atoms, such as, for example, methyl, ethyl, propyl, butyl, pentyl, hexyl, heptyl, octyl, nonyl, undecyl, decyl, dodecyl, octadecyl, nonadecyl, eicosyl, heneicosyl, docosyl, tricosyl, and the isomeric forms thereof; aryl groups having 6-25 carbon atoms, such as ring-substituted and ring-unsubstituted forms of phenyl, tolyl, xylyl, naphthyl, biphenyl, tetraphenyl, and the like; arylalkyl groups having 7-25 carbon atoms, such as ring-substituted and ring-unsubstituted forms of benzyl, phenethyl, phenpropyl, phenbutyl, naphthoctyl, and the like; and cycloalkyl groups, such as cyclopropyl, cyclobutyl, cyclopentyl, cyclohexyl, cycloheptyl, cyclooctyl, and the like. The term "aryl" as used herein refers to various forms of aryl groups that have been described hereinabove for the "hydrocarbyl" group. "Alkyl" refers to a straight or branched chain, saturated monovalent hydrocarbon group. Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a C2-6 alkanoyl group such as acyl); carboxamido; C1-6 or C1-3 alkyl, cycloalkyl, alkenyl, and alkynyl (including groups having at least one unsaturated linkages and from 2-8, or 2-6 carbon atoms); C1-6 or C1-3 alkoxys; C6-10 aryloxy such as phenoxy; C1-6 alkylthio; C1-6 or C1-3 alkylsulfinyl; C1-6 or C1-3 alkylsulfonyl; aminodi(C1-6 or C1-3)alkyl; C6-12 aryl having at least one aromatic rings (e.g., phenyl, biphenyl, naphthyl, or the like, each ring either substituted or unsubstituted aromatic); C7-19 arylalkyl having 1-3 separate or fused rings and from 6-18 ring carbon atoms; or arylalkoxy having 1-3 separate or fused rings and from 6-18 ring carbon atoms, with benzyloxy being an exemplary arylalkoxy.

The singular forms "a", "an", and "the" include plural referents unless the context clearly dictates otherwise. "Or" means "and/or". The modifier "about" used in connection with a quantity is inclusive of the stated value and has the meaning dictated by the context (e.g., includes the degree of error associated with measurement of the particular quantity).

The endpoints of all ranges directed to the same component or property are inclusive and independently combinable (e.g., ranges of "less than or equal to 25 wt %, or 5-20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. The suffix "(s)" is intended to include both the singular and the plural of the term that it modifies, thereby including at least one of that term (e.g., the colorant(s) includes at least one colorants). Unless defined otherwise, technical and scientific terms used herein have the same meaning as is commonly understood by one of skill in the art to which this invention belongs. A "combination" is inclusive of blends, mixtures, alloys, reaction products, and the like.

All publications, patents, and patent applications cited in this specification are herein incorporated by reference, and for any and all purposes, as if each individual publication, patent or patent application were specifically and individually indicated to be incorporated by reference. In the case of inconsistencies, the present disclosure will prevail.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method for the manufacture of a 2-aryl-3,3-bis (hydroxyaryl)phthalimidine of formula (I)

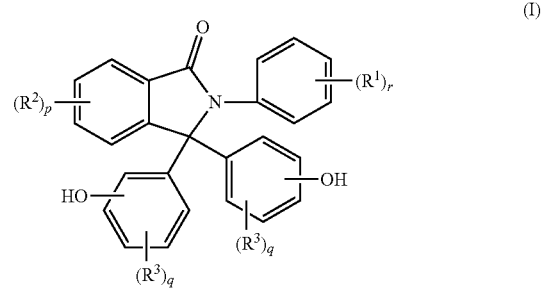

the method comprising:
continuously heating an anhydride of formula (II)

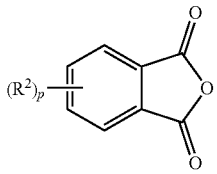
(II)

with a phenol of formula (III)

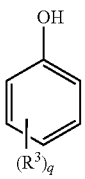
(III)

in the presence of a catalyst and a first co-catalyst, to form a first reaction mixture comprising a phenolphthalein compound of formula (IV)

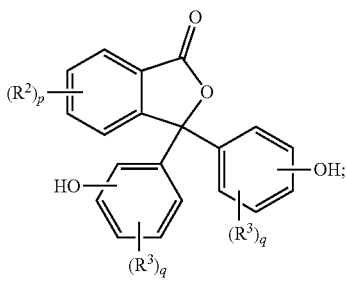
(IV)

continuously combining the first reaction mixture with sodium bisulfite and an organic solvent that is effective to dissolve the phenolphthalein compound of formula (IV) and thereby reduce the temperature of the first reaction mixture;
treating the first reaction mixture with a first adsorbent to provide a decolorized solution comprising the phenolphthalein compound of formula (IV);
precipitating the phenolphthalein compound of formula (IV) from the decolorized solution;
continuously combining a primary arylamine of formula (V)

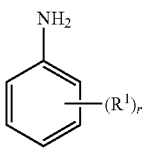
(V)

with an acid and a second co-catalyst to form a second reaction mixture;
adding the phenolphthalein compound of formula (IV) to the second reaction mixture;

continuously heating the second reaction mixture to provide a third reaction mixture comprising a crude phthalimidine of formula (I);
continuously combining the third reaction mixture with an aqueous base to form a first aqueous stream;
continuously extracting the first aqueous stream with an aminoaryl compound of formula (VI)

$(R^4)(R^5)N—Ar(R^6)_s$ (VI)

to provide an organic stream and a second aqueous stream comprising the crude phthalimidine of formula (I);
continuously removing the aminoaryl compound of formula (VI) from the second aqueous stream to provide a third aqueous stream;
continuously contacting the third aqueous stream with a second adsorbent to provide a fourth aqueous stream;
continuously precipitating the phthalimidine of formula (I) from the fourth aqueous stream to provide a slurry;
continuously concentrating the slurry and separating a wet solid comprising the phthalimidine of formula (I) from the concentrated slurry;
continuously triturating the wet solid comprising the phthalimidine of formula (I) with an aqueous methanol solution to provide a triturated solid comprising the 2-aryl-3,3-bis(hydroxyaryl)phthalimidine of formula (I); and
isolating the triturated solid to provide a purified 2-aryl-3,3-bis(hydroxyaryl)phthalimidine of formula (I),
wherein in formulas (I), (II), (III), (IV), (V), and (VI)
each occurrence of $R^1$ is independently a phenyl or a $C_{1-25}$ hydrocarbyl,
each occurrence of $R^2$ and $R^3$ is independently a $C_{1-25}$ hydrocarbyl or halogen,
each $R^4$ and $R^5$ is independently a hydrogen or $C_{1-25}$ hydrocarbyl,
Ar is a $C_{6-12}$ aromatic ring optionally comprising up to three heteroatoms in the ring,
each $R^6$ is independently a halogen, nitro, cyano, or $C_{1-25}$ hydrocarbyl, and
r, p, q, and s are each independently 0- to 4.

2. The method of claim 1, wherein
the anhydride of formula (II) is phthalic anhydride,
the phenol of formula (III) is phenol,
the catalyst is zinc chloride, aluminum chloride, stannic chloride, hydrochloric acid, sulphuric acid, methanesulfonic acid, or a combination thereof, and
the first co-catalyst is chlorosulfonic acid, trichloroacetic acid, methanesulfonic acid, dodecylbenzenesulfonic acid, triflic acid, boron trifluoride, p-toluene sulphonyl chloride, or a combination thereof.

3. The method of claim 1, wherein the heating of the first reaction mixture is at 100-150° C.

4. The method of claim 1, wherein the heating of the first reaction mixture is for 4- to 10 hours.

5. The method of claim 1, wherein the precipitating the phenolphthalein compound of formula (IV) comprises at least partially removing the organic solvent to form a slurry, and cooling the slurry.

6. The method of claim 1, further comprising washing the precipitated phenolphthalein compound of formula (IV).

7. The method of claim 1, further comprising drying the precipitated phenolphthalein compound of formula (IV).

8. The method of claim 1, wherein the primary arylamine of formula (V) is aniline, the acid catalyst is a mineral acid, and the second co-catalyst is a heterocyclic aromatic amine.

9. The method of claim 1, wherein the heating of the second reaction mixture is from 155- to 185° C.

10. The method of claim 1, wherein the heating of the second reaction mixture is for 5- to 15 hours.

11. The method of claim 1, wherein the phenol of formula (III) is present at a concentration of greater than 2 molar equivalents of the anhydride of formula (II).

12. The method of claim 1, further comprising
combining the acid and the primary arylamine of formula (V) to form an initial second reaction mixture;
removing water from the initial second reaction mixture to provide a reduced water second reaction mixture; and
adding the phenolphthalein compound of formula (IV) and the second co-catalyst to the reduced water second reaction mixture to provide the second reaction mixture.

13. The method of claim 1, comprising
combining the phenolphthalein compound of formula (IV) and the primary arylamine of formula (V) to form a combined reaction mixture; and
removing water from the combined reaction mixture to a level of less than 4 wt %.

14. The method of claim 1, further comprising recycling the aminoaryl compound of formula (VI) from the organic stream.

15. The method of claim 1, wherein removing the residual aminoaryl compound of formula (VI) from the second aqueous stream comprises azeotropic distillation or extraction with ethylene dichloride.

16. The method of claim 1, wherein the isolating comprises continuous crystallization.

17. The method of claim 1, wherein the 2-aryl-3,3-bis(hydroxyaryl)phthalimidine of formula (I) is of formula (IA)

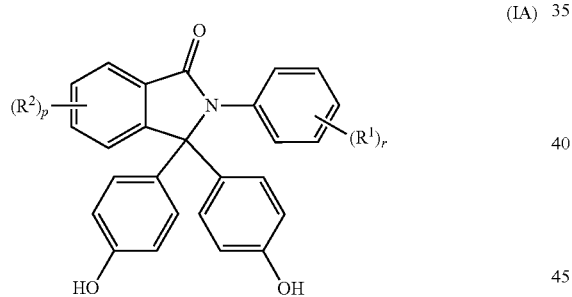

(IA)

wherein R$^1$ is a C$_{1-3}$ alkyl, R$^2$ is a C$_{1-3}$ alkyl or a halogen, p is 0 or 1, and r is 0 or 1.

18. The method of claim 17, wherein each of q, p and r 0, and the phthalimidine of formula (I) is 2-phenyl-3,3-bis(4-hydroxyphenyl)-2-phthalimidine of formula (IB)

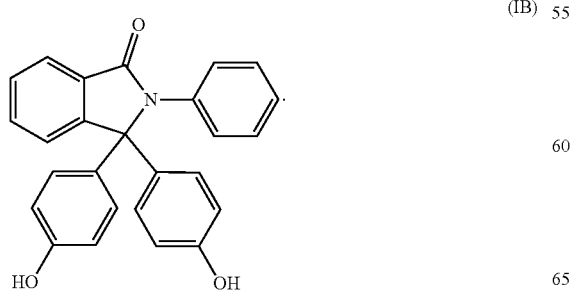

(IB)

19. A method for the manufacture of a 2-phenyl-3,3-bis(4-hydroxyphenyl)-2-phthalimidine of formula (IB)

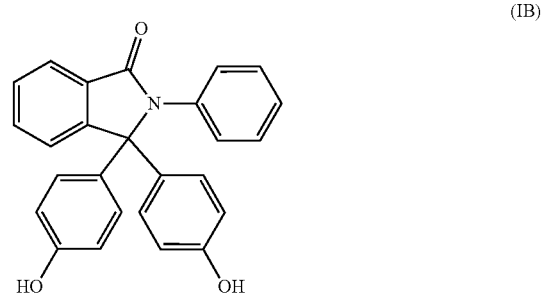 [SMILES: O=C1c2ccccc2C(c2ccc(O)cc2)(c2ccc(O)cc2)N1c1ccccc1]

(IB)

the method comprising:
continuously heating phthalic anhydride with phenol in the presence of zinc chloride and chlorosulfonic acid at 100- to 150° C. for 4- to 10 hours, to form a first reaction mixture comprising a phenolphthalein compound;
continuously combining the first reaction mixture with sodium bisulfite and an organic solvent that is effective to dissolve the phenolphthalein compound and thereby reduce the temperature of the first reaction mixture;
treating the first reaction mixture with activated carbon to provide a decolorized solution;
precipitating the phenolphthalein compound from the decolorized solution by at least partially removing the organic solvent to form a slurry, and cooling the slurry;
continuously combining aniline with hydrochloric acid and pyridine or 4-dimethylamino pyridine to form a second reaction mixture;
adding the phenolphthalein compound to the second reaction mixture;
continuously heating the second reaction mixture at 155- to 185° C. for 5- to 15 hours to provide a third reaction mixture comprising a crude phthalimidine of formula (IB);
continuously combining the third reaction mixture with sodium hydroxide to form a first aqueous stream;
continuously extracting the first aqueous stream with aniline to provide an organic stream and a second aqueous stream comprising the crude phthalimidine of formula (IB);
continuously removing the aniline from the second aqueous stream to provide a third aqueous stream;
continuously contacting the third aqueous stream with activated charcoal carbon to provide a fourth aqueous stream;
continuously precipitating the phthalimidine of formula (IB) from the fourth aqueous stream to provide a slurry;
continuously concentrating the slurry and separating a wet solid comprising the phthalimidine of formula (IB) from the concentrated slurry;
continuously triturating the wet solid comprising the phthalimidine of formula (IB) with an aqueous methanol solution to provide a triturated solid comprising the 2-aryl-3,3-bis(hydroxyaryl)phthalimidine of formula (IB); and continuously isolating the triturated solid to provide a purified 2-aryl-3,3-bis(hydroxyaryl)phthalimidine of formula (IB).

20. A method for the manufacture of a polycarbonate, comprising manufacturing a 2-aryl-3,3-bis(4-hydroxyaryl) phthalimidine of formula (I)

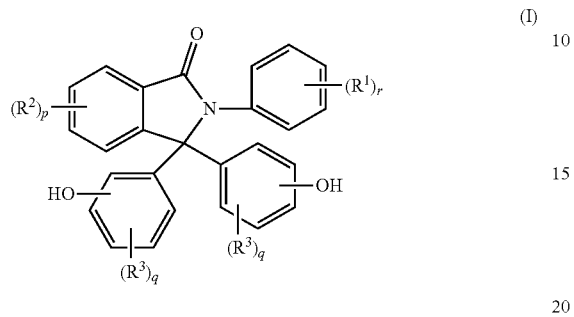

the method comprising:
continuously heating an anhydride of formula (II)

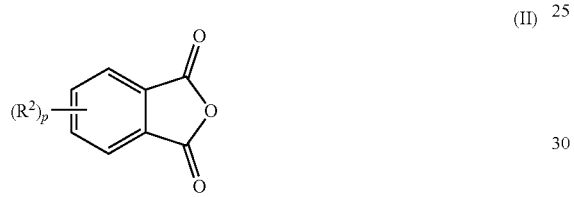

with a phenol of formula (III)

in the presence of a catalyst and a first co-catalyst, to form a first reaction mixture comprising a phenolphthalein compound of formula (IV)

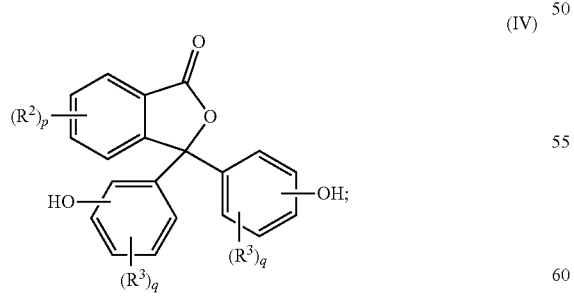

continuously combining the first reaction mixture with sodium bisulfite and an organic solvent that is effective to dissolve the phenolphthalein compound of formula (IV) and thereby reduce the temperature of the first reaction mixture;

treating the first reaction mixture with a first adsorbent to provide a decolorized solution comprising the phenolphthalein compound of formula (IV);

precipitating the phenolphthalein compound of formula (IV) from the decolorized solution;

continuously combining a primary arylamine of formula (V)

with an acid and a second co-catalyst to form a second reaction mixture;

adding the phenolphthalein compound of formula (IV) to the second reaction mixture;

continuously heating the second reaction mixture to provide a third reaction mixture comprising a crude phthalimidine of formula (I);

continuously combining the third reaction mixture with an aqueous base to form a first aqueous stream;

continuously extracting the first aqueous stream with an aminoaryl compound of formula (VI)

$(R^4)(R^5)N—Ar(R^6)_s$ (VI)

to provide an organic stream and a second aqueous stream comprising the crude phthalimidine of formula (I);

continuously removing the aminoaryl compound of formula (VI) from the second aqueous stream to provide a third aqueous stream;

continuously contacting the third aqueous stream with a second adsorbent to provide a fourth aqueous stream;

continuously precipitating the phthalimidine of formula (I) from the fourth aqueous stream to provide a slurry;

continuously concentrating the slurry and separating a wet solid comprising the phthalimidine of formula (I) from the concentrated slurry;

continuously triturating the wet solid comprising the phthalimidine of formula (I) with an aqueous methanol solution to provide a triturated solid comprising the 2-aryl-3,3-bis(hydroxyaryl)phthalimidine of formula (I); and isolating the triturated solid to provide a purified 2-aryl-3,3-bis(hydroxyaryl)phthalimidine of formula (I), wherein in formulas (I), (II), (III), (IV), (V), and (VI)
each occurrence of $R^1$ is independently a phenyl or a $C_{1-25}$ hydrocarbyl,
each occurrence of $R^2$ and $R^3$ is independently a $C_{1-25}$ hydrocarbyl or halogen,
each $R^4$ and $R^5$ is independently a hydrogen or $C_{1-25}$ hydrocarbyl,
Ar is a $C_{6-12}$ aromatic ring optionally comprising up to three heteroatoms in the ring,
each $R^6$ is independently a halogen, nitro, cyano, or $C_{1-25}$ hydrocarbyl, and
r, q, and s are each independently 0 to 4,
and
polymerizing the 2-aryl-3,3-bis(4-hydroxyaryl) phthalimidine of formula (I) in the presence of a carbonate source.

* * * * *